(12) United States Patent
Gagnon et al.

(10) Patent No.: US 8,750,587 B2
(45) Date of Patent: Jun. 10, 2014

(54) METHOD AND SYSTEM FOR PET IMAGE RECONSTRUCTION USING PORTION OF EVENT DATA

(75) Inventors: Daniel Gagnon, Twinsburg, OH (US); Jeffrey A. Kolthammer, Lyndhurst, OH (US)

(73) Assignee: Koninklijke Philips N.V., Eindhoven (NL)

( * ) Notice: Subject to any disclaimer, the term of this patent is extended or adjusted under 35 U.S.C. 154(b) by 1028 days.

(21) Appl. No.: 12/091,752

(22) PCT Filed: Oct. 30, 2006

(86) PCT No.: PCT/IB2006/054013
§ 371 (c)(1),
(2), (4) Date: Apr. 28, 2008

(87) PCT Pub. No.: WO2007/052211
PCT Pub. Date: May 10, 2007

(65) Prior Publication Data
US 2008/0285828 A1 Nov. 20, 2008

Related U.S. Application Data

(60) Provisional application No. 60/596,955, filed on Nov. 1, 2005.

(51) Int. Cl.
*A61B 6/03* (2006.01)

(52) U.S. Cl.
CPC ..................................... *A61B 6/037* (2013.01)
USPC ......................................................... 382/131

(58) Field of Classification Search
CPC ................ G01T 1/2985; G06T 11/006; G06T 2211/424; G06T 2211/428; G06T 2207/10104; A61B 6/037; A61B 6/488; A61B 6/5205; G01V 5/085; H03M 1/10

USPC .............................. 382/128–134; 250/363.03
See application file for complete search history.

(56) References Cited

U.S. PATENT DOCUMENTS

| 7,489,799 | B2 * | 2/2009 | Nilsen et al. ................. 382/100 |
| 2004/0170246 | A1 | 9/2004 | Koenig et al. | |

FOREIGN PATENT DOCUMENTS

| JP | 2005101720 | | 4/2005 |
| WO | 2007039841 | A2 | 4/2007 |
| WO | 2007046013 | A2 | 4/2007 |

OTHER PUBLICATIONS

Rahmim et al., Statistical list-mode image reconstruction for the high resolution research tomograph, Aug. 27, 2004, Physics in Medicine and Biology, vol. 49, pp. 4239-4258.*

(Continued)

*Primary Examiner* — Toan Ton
*Assistant Examiner* — John Corbett

(57) ABSTRACT

A method and system for use in positron emission tomography, wherein a list-based reconstructor means (129) is configured to generate first portion volumetric data responsive to a first portion of a plurality of positron annihilation events detected during a positron emission tomography scan; generate a human-readable image indicative of the first portion volumetric data; use a list-based reconstruction technique to generate composite volumetric data responsive to the first portion volumetric data and a second portion of the plurality of positron annihilation events; and generate a composite human-readable image indicative of the composite volumetric data. In another aspect the reconstructor (129) is configured to selecting first or second portion event quantities responsive to one or more parameters including image definition requirements and processing time requirements.

24 Claims, 2 Drawing Sheets

(56) References Cited

OTHER PUBLICATIONS

Figure 1:
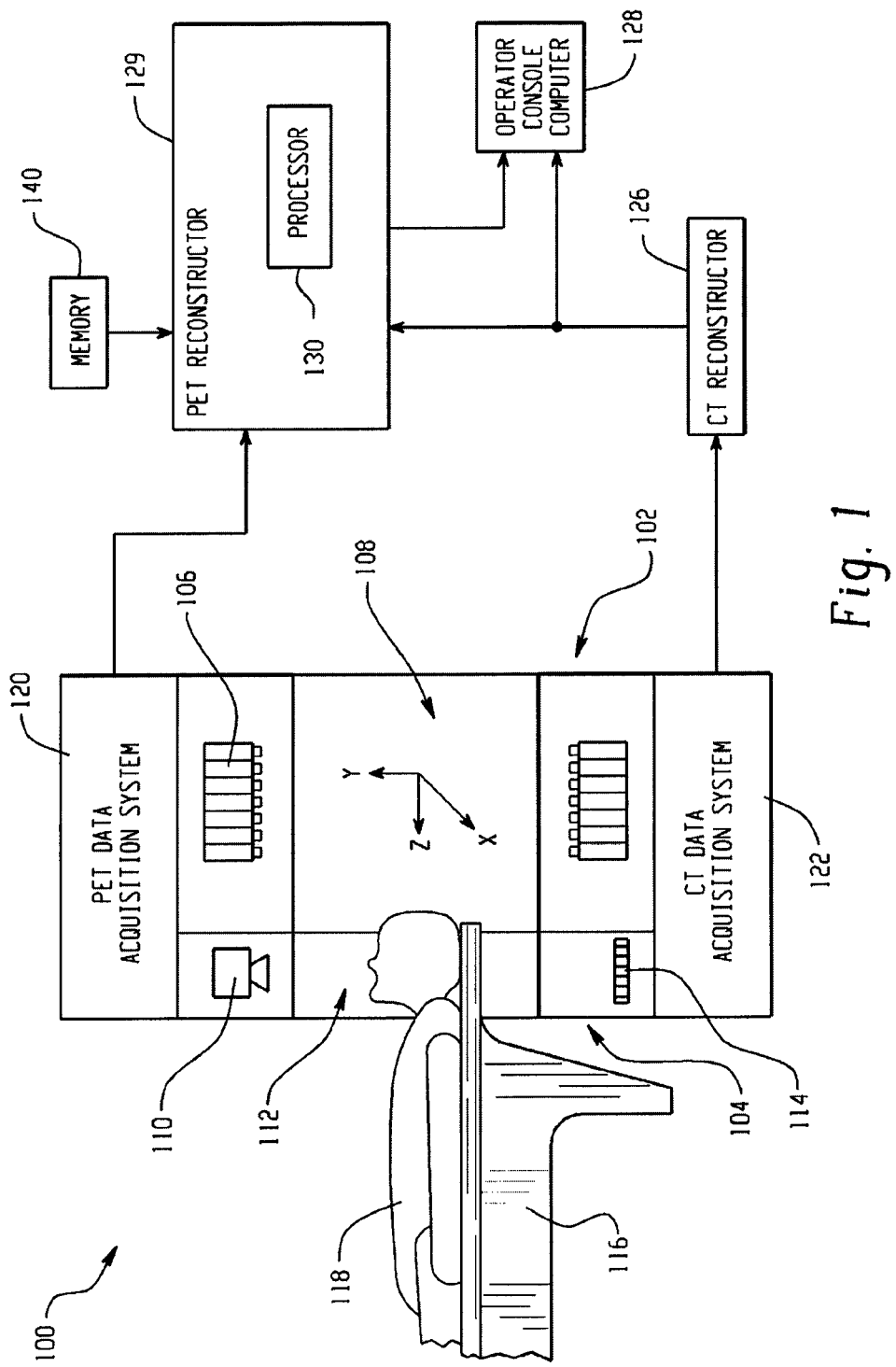

Selivanov et al., Real-Time PET Image Reconstruction Based on regularized Pseudo-Inverse of the System Matrix, Aug. 2, 2002, 2001 IEEE Nuclear Science Symposium Conference Record, pp. 1737-1741.*

Reader et al., Accelerated List-Mode EM Algorithm, 2002, IEEE Transactions on Nuclear Science, vol. 49, No. 1, pp. 42-49.*

Rahim, A. et al., "Statistical List-Mode Image Reconstruction for the High Resolution Research Tomograph," Physics in Medicine and Biology, Taylor and Francis Ltd., London, GB, 2004, 49(18), pp. 4239-4258.

Hudson, H.M., et al., "Accelerated Image Reconstruction Using Ordered Subsets of Projection Data," IEEE Transactions on Medical Imaging, IEEE Service Center, Piscataway, NJ, 1994, 13(4), pp. 601-609.

Written Opinion of the International Searching Authority dated May 6, 2008; for Int. Appln. No. PCT/IB2006/054013.

* cited by examiner

METHOD AND SYSTEM FOR PET IMAGE RECONSTRUCTION USING PORTION OF EVENT DATA

CROSS REFERENCE TO RELATED APPLICATIONS

This application claims the benefit of U.S. provisional application Ser. No. 60/596,955 filed Nov. 1, 2005, which is incorporated herein by reference.

The present invention relates to the field of positron imaging, and more particularly to the reconstruction of data acquired in positron emission tomography (PET).

Positron emission tomography (PET) is a branch of nuclear medicine in which a positron-emitting radiopharmaceutical such as 18F-fluorodeoxyglucose (FDG) is introduced into the body of a patient. As the radiopharmaceutical decays, positrons are generated. More specifically, each of a plurality of positrons reacts with an electron in what is known as a positron annihilation event, thereby generating a coincident pair of 511 keV gamma rays which travel substantially in opposite directions along a line of coincidence. A gamma ray pair detected within a coincidence time is ordinarily recorded by the PET scanner as an annihilation event. Data from a plurality of annihilation events is used to reconstruct or create images of the patient or object scanned. More particularly, the reconstructed images provide information about the distribution of the radionuclide in the object.

As computing power has increased PET reconstruction techniques have progressed through analytical backprojection and statistical (iterative) techniques to direct, crystal-space reconstruction in which detection measurements are used directly in reconstruction. One reconstruction technique that has thus far received limited attention due to its impact on computational load is the event-based or event-by-event technique. The use of event-based reconstruction techniques is attractive from an information flow point of view where a pipeline of operation from detection to final image can be defined. Moreover, event-based reconstruction techniques are particularly suitable for PET reconstruction responsive to event time-of-flight ("TOF") or depth-of-interaction encoded data.

In TOF imaging the time within the coincidence interval at which each gamma ray in an event coincident pair is detected is measured, providing an indication of a location of a detected event along its line of coincidence. This additional level of spatial location specificity provides reconstruction advantages over other non-TOF reconstruction techniques, more particularly by providing improved image definitions.

However, event-based reconstruction techniques typically require much heavier computational requirements than histogram based or other reconstruction techniques, especially when the reconstruction includes TOF data. The heavier computational requirements generally result in corresponding increases in processing times and overall image generation times.

On the other hand, users generally prefer to have image information available as soon as possible following a scan. From a workflow point of view, for example, it is desirable to evaluate whether a particular scan covered the desired region or regions of interest or was otherwise successful while the patient is still in the vicinity of the scanner. Such an evaluation does not typically require a diagnostic quality image.

Therefore, what is needed is an improved event-based PET reconstruction process, optionally responsive to TOF event information that provides for extraction of intermediate data from the process to confirm that a successful study has been completed and that the final image is being prepared, without causing computational or processing time requirement disadvantages. What is also needed is a method and system for producing faster final reconstruction images through efficient use of event list data.

Aspects of the present invention address these matters, and others. More particularly a method and system is provided for use in positron emission tomography, wherein a list-based reconstructor is configured to generate first portion volumetric data responsive to a first portion of a plurality of positron annihilation events detected during a positron emission tomography scan; generate a human-readable image indicative of the first portion volumetric data; use a list-based reconstruction technique to generate composite volumetric data responsive to the first portion volumetric data and a second portion of the plurality of positron annihilation events; and generate a composite human-readable image indicative of the composite volumetric data. In another aspect the reconstructor is configured to selecting first and/or second portion event quantities responsive to one or more parameters, illustratively including image definition requirements and processing time requirements. In another aspect the composite volumetric data may be generated by using the first portion volumetric data as an initial image estimate and updating the initial image estimate responsive to the second event portion.

FIG. 1 depicts a combined PET/CT system.

Figure 2:
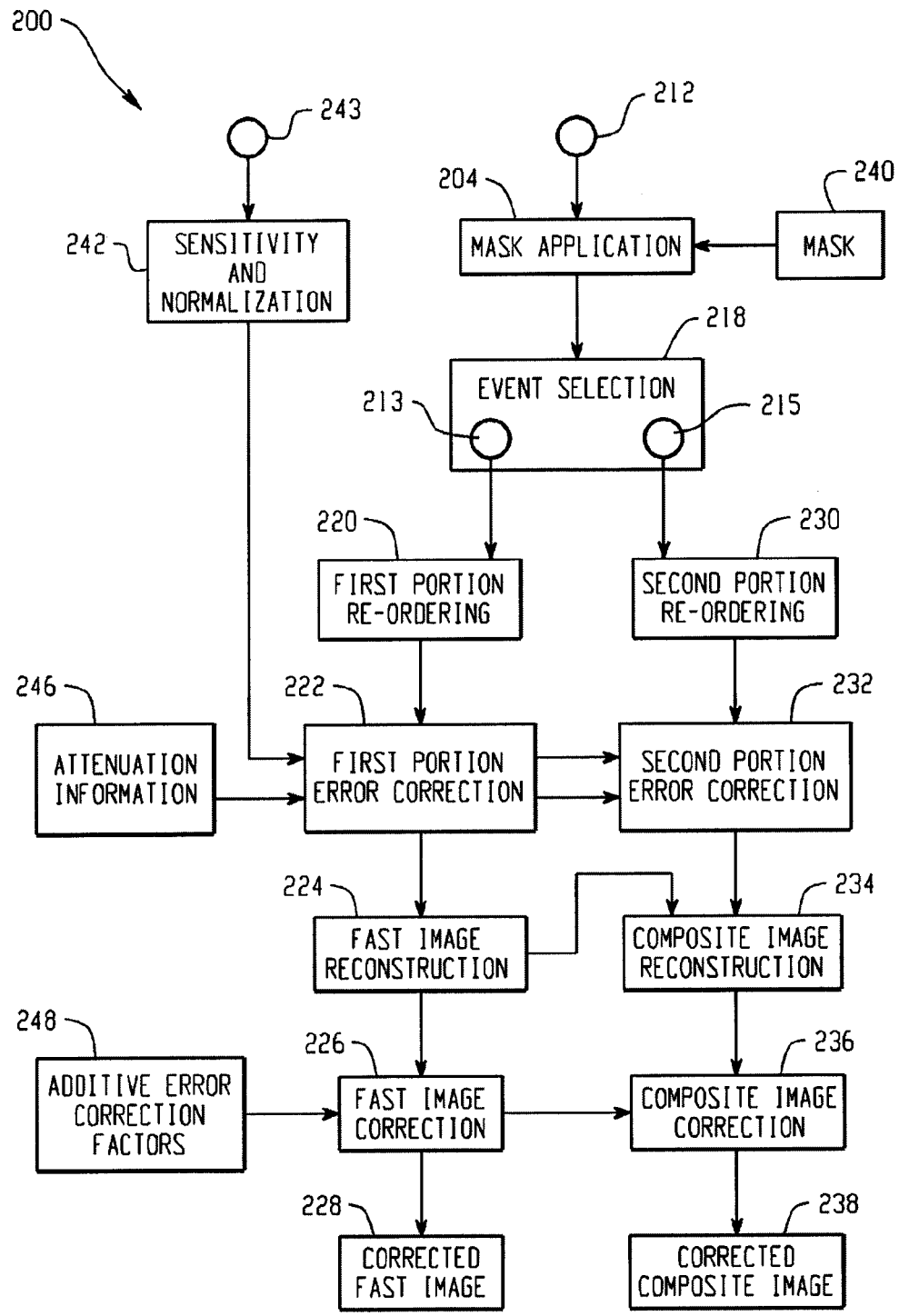

FIG. 2 provides a flow chart of a method according to the present invention.

With reference to FIG. 1, a combined PET/CT system 100 includes a PET gantry portion 102 and a CT gantry portion 104. The PET gantry portion 102 includes one or more axial rings of radiation sensitive detectors 106 which surround an examination region 108. The detectors 106 detect gamma radiation characteristic of positron annihilation events occurring within a PET examination region 108.

The CT portion 104 includes a radiation source 110 such as an x-ray tube which rotates about a CT examination region 112. Radiation sensitive detectors 114 detect radiation emitted by the x-ray source which has traversed the examination region 112.

The PET gantry portion 102 and CT gantry portion 104 are preferably located in proximity with their respective examination regions 108, 112 disposed along a common longitudinal or z-axis. An object support 116 supports an object to be imaged 118, such as a human patient. The object support 116 is preferably longitudinally movable in coordination with operation of the PET/CT system 100 so that the object 118 can be scanned at a plurality of longitudinal locations by both the PET and CT gantry portions 102, 104.

A CT data acquisition system 122 processes the signals from the CT detectors 114 to generate data indicative of the radiation attenuation along a plurality of lines or rays through the examination region 112. A CT reconstructor 126 reconstructs the data using suitable reconstruction algorithms to generate volumetric image data indicative of the radiation attenuation of the object 118.

A PET data acquisition system 120 provides projection data which includes a list of annihilation events detected by the detectors 106. More particularly, the projection data may also provide TOF information.

A PET reconstructor 129 includes at least one computer or computer processor 130, which includes at least one central processing unit (CPU) or processor. Suitable architectures may include one or more proprietary computers and dedicated hardware implementations. Generally speaking, the use of additional or more powerful processors will reduce total reconstruction times.

The PET reconstructor 129 generates volumetric image data indicative of the distribution of the radionuclide in the object 118. In addition, the PET reconstructor 129 preferably uses information from the CT reconstructor 126 to apply attenuation and other desired corrections to the PET data. Computer readable instructions which cause the processor(s) 130 to carry out the reconstruction are preferably carried on one or more computer readable media 140 such as computer disks, volatile or non-volatile memory, or the like; and the computer readable instructions may also be transmitted by way of a suitable communications network such as the internet to storage media 140 accessible to the processor(s) 130.

A workstation computer serves an operator console 128. The console 128 includes a human readable output device such as a monitor or display and input devices such as a keyboard and mouse. Software resident on the console 128 allows the operator to view and otherwise manipulate the volumetric image data generated by the PET and CT reconstructors 129 and 126. Software resident on the console 128 also allows the operator to control the operation of the system 100 by establishing desired scan protocols, initiating and terminating scans, and otherwise interacting with the scanner. Reconstructed image data may also be made available to other computers associated with the system 100 or otherwise having access to a common network such as a picture archiving and communication (PACS) system, hospital information system/radiology information system (HIS/RIS) system, the internet, or the like.

Variations on the system 100 are also possible. Thus, for example, the CT portion of the scanner may be omitted, located remotely from the PET gantry portion 102, or replaced with another imaging device such as a magnetic resonance (MR) scanner. Alternately, attenuation or anatomical information may be provided by a transmission source associated with the PET gantry portion 102.

Turning now to FIG. 2, a reconstruction method 200 performed by the PET reconstructor will be described in greater detail. At 212, the reconstructor receives list mode event data produced by PET scanner as result of a scan. In a process step 204 anatomic mask information 240 is applied to PET event data. More particularly, the anatomic mask information 240 is applied to eliminate annihilation events detected outside of scanned object boundaries. Since reconstruction times on event-mode data are generally proportional to the total number of events to be processed, the elimination of events reduces total reconstruction time. However, it is to be understood that anatomic masking to the PET data 212 is optional, and alternative embodiments may not apply anatomic masking to the PET data 212.

At 218, the plurality of detected events are split into a first portion 213 and a second portion 215, where the first portion includes X % of the events, and the second portion 215 chosen from the remainder of the events, accordingly comprising less than or equal to (100−X) % of the events. Events may be selected for each of the first and second portions through a variety of bases, including for example random, geometric and numerically based sampling (such as every nth event) techniques. Generally, the first and second portions are defined in such a way that they do not carry any biases with respect to geometry or time so that they can be reconstructed independently. In one aspect, where a scan acquisition time is substantially short with respect to isotope decay, one simple approach is the take every nth event in the event list 212 to create the first and second portions; however, it is to be understood that other techniques can also be applied. For instance, when the object/patient 118 is not moving continuously, and the scan acquisition is performed in a step-and-shoot manner, segmenting the scan acquisition time per position into a desired ratio is perfectly appropriate.

In step 220 the first portion 213 events are optionally reordered. In step 222 error corrections are performed on the first portion 213 events responsive to attenuation information 246 and scanner-specific sensitivity and normalization information 242. Attenuation correction is generally applied in PET image reconstruction to achieve count values independent from object tissue densities. Accordingly the CT reconstructor 126 provides attenuation information 246 indicative of the radiation attenuation of the scanned object 118. Alternatively, other techniques for obtaining the attenuation information 246 may also be implemented: for example, attenuation or anatomical information may be provided by a transmission source associated with the PET gantry portion 102.

The sensitivity and normalization correction information 242 is derived from scanner specific corrections based on PET scanner system performance parameters 243. Parameter 243 examples include coefficients related to detector crystal efficiency, normalization, detector geometry, detector crystal decay time, and dead time constants. In one example, observing that an individual PET detector 106 is not operational or has lost some sensitivity may result in a constant performance modifier to be applied to detection data reported by that detector 106.

In step 224 the first portion 213 data as preprocessed and corrected in steps 220 and 222 is reconstructed to provide first portion volumetric data indicative of the radionuclide distribution in the object under examination. Although other reconstruction techniques may be practiced, one appropriate reconstruction technique is the maximum likelihood expectation maximization (MLEM) technique.

At 226 the first portion volumetric data is corrected for additive error corrections responsive to additive error correction factors 248. Additive event data error corrections, for example scatters and randoms, generally address low frequency errors, such that a high degree of spatial resolution is not essential for their responsive correction. And reconstructed volumetric images are generally defined by a lower number of discrete volumetric elements, such as voxels or blobs, relative to the original plurality of events they are reconstructed from. Accordingly, in another aspect reduced image generation times are accomplished by performing additive error corrections responsive to the additive error correction factors 248 on the first portion volumetric data image space elements, rather than applying additive error correction to the relatively larger plurality of first portion event data.

The corrected first portion image reconstruction is then made available for display in step 228. Thus an image may be reconstructed and displayed responsive to a portion of a totality of a plurality of PET events on a faster basis relative to the reconstruction and display of an image responsive to the totality of PET events. This faster total image reconstruction and display characteristic thus enables display of the first portion image during processing of the totality of event image, therefore intermediate to the processing and display of an image responsive to the totality of events. Thus the first event portion-responsive intermediate display in step 228 may be used to confirm a successful object scan prior to a final corrected composite image reconstruction and display in step 238, as will be described presently.

Referring now to the processing and reconstruction of the second portion of events 215 selected in step 218, the second portion events 215 are reordered at step 230, and corrected responsive to the attenuation correction information 246 and the event-level error correction information 242 in step 232, as described generally above with respect to the first portion reordering and error correction steps 220, 222. Optionally, the process 200 may be configured to perform the first portion reordering and error correction steps 220, 222 in advance of the second portion reordering and error correction steps 230, 232: the first portion error correction step 222 output may then be utilized directly in the second portion error correction step 232 for re-weighting of the second portion events 215, thus providing additional processing time advantages.

Alternatively, either or both of the second portion reordering and error correction steps 230, 232 may be omitted. The composite image reconstruction step 234 may thus reconstruct the second portion 215 without pre-processing through reordering and/or correcting the individual second portion events 215. Instead, the second portion events 215 may be reconstructed responsive to correction parameters provided by the first portion reconstruction step 224. The step 224 correction parameters may include one or more of reordering, attenuation and event-level error data correction parameters.

At step 234 composite image volumetric data is reconstructed responsive to the both the first portion of events 213 and the second portion of events 215. In another aspect the first portion volumetric data may be used as an initial image estimate iteration for the step 234 composite image reconstruction, thus reducing overall composite image reconstructor step 234 reconstruction processing times. Step 234 composite image volumetric data may therefore be generated responsive to the first portion reconstructor 224 volumetric data updated through at least one successive image estimate iteration responsive to the second event portion 215.

At 236 additive error corrections are performed on the composite image volumetric data generated in step 234. More particularly, additive error correction is performed on the volumetric data reconstructed from the second event portion 215 at step 234, in a fashion similar to the process described at step 226. In another aspect, the composite image correction step 236 may comprise application of step 226 additive-error correction information to the step 234 second portion image output, wherein the step 226 additive-error correction information is determined from correcting the first portion image output of step 224. According to one technique described in a commonly-assigned provisional U.S. application by Gagnon et al for "Method & System for List-Mode PET Reconstruction using a Surrogate Image", filed on Oct. 5, 2005, application Ser. No. 60/596,587 and since published as US 2008/0253640 A1 on Oct. 16, 2008, the entire disclosure of which is hereby incorporated by reference, where image space reconstructions are defined by image space elements (such as voxels or blobs), the step 226 additive-error correction information comprises "element correction factors" determined by processing the step 224 first portion image output responsive to the additive error correction factors 248. Each image space element has a parameter representing the contribution of scatters; another parameter representing the contributions of randoms; and optionally additional parameters, one for each additional additive error correction contemplated. Thus the image element correction factors are determined through processing only X % of the totality of events reconstructed, the image element correction factors then applied directly to the image elements reconstructed from the second portion events. Thus a faster process is provided as compared to techniques requiring determination of additive error image element corrections through processing all reconstruction image elements.

A final composite image is then created by combining the corrected first and second portion image space reconstructions, and made available for display in step 238.

In one aspect the percentage size X of the first portion 213 may be chosen responsive to system performance objectives. In one example configured to generate a fast intermediate reconstructed human-readable output device image from a first portion 213 comprising TOF data, X is selected as 25%. Compared to non-TOF-responsive reconstruction techniques, event-based TOF-responsive reconstruction generally reduces twice the reconstruction estimation variances caused by noise. And reducing the number of events by a factor of four should result in only a two-fold increase in the level of noise relative to an image reconstructed from 100% of the events. Therefore, a TOF-responsive reconstruction based upon the first portion 213 of 25% of events may be utilized to generate a first portion image comparable in definition to a non-TOF image reconstruction from 100% of the events, but generated four-times faster than the complete event list reconstruction. Accordingly, an "intermediate" image may be reconstructed for processing and display upon the console 128 human readable output device (as more fully described below) responsive to a first portion of events 213 where X=25%, the image of a suitable definition for display and review to confirm a successful object scan.

Other first portion 213 percentage size X values may be chosen based upon desired objectives. In general, higher X values will provide higher definition intermediate images having longer image generation times, and lower X percentage values will provide lower definition intermediate images having faster image generation times. Thus the percentage X may be any value deemed suitable by an end user based upon needs and objectives, and is not restricted to 25%.

In another aspect, faster composite image generation may be accomplished by selecting only a portion of the totality of PET events 212 for composite image processing and reconstruction. More particularly, in an alternative embodiment of the process 200, in step 218 a composite image portion of Y % is selected, Y<100% of the plurality of detected events 212, for use for composite image processing, reconstruction and display through the composite image path defined by steps 230/232/234/236/238. The second portion 215 event count is thus defined as Y−X.

In this fashion some event counts are discarded in order to reduce total composite image processing times. However, although composite image definition may be reduced relative to a composite image reconstructed from 100% of the plurality of detected events 212, a resultant composite image may still have an adequate image definition. For example, where composite image volumetric data is reconstructed responsive to a Y portion of TOF event data 212 at step 234, volumetric data generated responsive to less than a totality of the event data 212 may nonetheless have an equivalent, or even higher definition, than that obtainable through a non-TOF responsive reconstruction technique responsive to all of the events 212.

In one aspect a composite image portion size Y of less than the total event 212 count may be chosen responsive to one or more system performance objectives. According to one technique described in a commonly-assigned provisional U.S. application by Narayanan et al for "Patient Scan Time Optimization for PET/SPECT Imaging", filed on Oct. 18, 2005, application Ser. No. 60/727,799 and since published as US 2009/0171183 A1 on Jul. 2, 2009, the entire disclosure of which is hereby incorporated by reference, the acquisition of event counts of an object scanned may be stopped responsive to the realization of a certain goal. For example, in this fashion Y may be chosen responsive to an overall acquisition time objective, such as a desire to minimize the time that an object/patient 118 is required to remain on the object support imaging table 116.

In another aspect Y may be chosen responsive to one or more configuration parameters, such as a TOF variance improvement factor (as compared to a LOR-histogram technique image capability), or a specified time constraint for generating a corrected composite image in step 238. In another aspect Y may be determined mathematically responsive to a selected TOF first portion fast intermediate image variance improvement factor and a specified composite image total generation time.

In another aspect the first portion data set 213 size X may be chosen as a function of Y, thus providing for a reduction in total first portion data 213 event counts and a correspondingly faster intermediate image processing and display times where Y<100% of total events 212. Thus composite image portion Y sampling may be used to provide both faster intermediate and composite image processing and display times through reducing the size of the first portion data set 213 size X.

In another aspect the first portion data set 213 size X and composite image portion size Y may be chosen responsive to both fast intermediate image generation and fast composite image generation objectives. For example, a preferred first portion percentage X of a given total event count may be chosen responsive to an intermediate image quality requirement, and Y chosen responsive to the value of X. The total event rate processed for display in step 238 would then be Y of the incoming PET data 212 counts. In another aspect the first portion data set 213 size may chosen equal to the product of X and Y, satisfying both the need for a fast initial intermediate image and a prompt composite image of acceptable quality.

In one aspect an embodiment of the invention described above is tangibly embodied in a computer program stored in suitable memory storage device 140 and made available to the system 100 and reconstructor 129. Exemplary machine-readable memory 140 storage mediums include, but are not limited to, fixed hard drives, optical discs, magnetic tapes, semiconductor memories, such as read-only memories (ROMs), programmable (PROMs), etc. The memory 140 containing the computer readable code is utilized by executing the code directly from the memory 140, or by copying the code from one memory storage device to another memory storage device, or by transmitting the code on a network for remote execution. The memory 140 may comprise one or more of a fixed and/or removable data storage device such as a floppy disk or a CD-ROM, or it may consist of some other type of data storage or data communications device. The computer program may thus configure the processor 130 for execution of the techniques described above. The computer program comprises instructions which, when read and executed by a processor 130 causes the processor 130 to perform the steps necessary to execute the steps or elements of the present invention.

While embodiments of the invention have been described herein, variations in the design may be made, and such variations may be apparent to those skilled in the art of positron imaging, coincidence detection and emission tomography systems and methods, as well as to those skilled in other arts. It will be readily apparent that the techniques described above may be practiced by single, multiple or networked computers. In one embodiment one reconstructor processor 130 may perform all of process steps 218, 220, 222, 224, 226, 228, 230, 232, 234, 236, and 238 described above. Similarly one display device associated with the computer console may function to display both the corrected fast intermediate image at step 228 and the corrected composite image at step 238.

In another aspect embodiment two or more reconstruction processors 130 may be provided within the reconstructor 129, wherein one reconstruction processor 130 is configured to select the first and composite image event portions at step 218. In one example a first reconstruction processor 130 is further configured to perform the fast intermediate image path steps 220/222/224/226/228 temporally in parallel with composite image path steps 230/232/234/236/238 performed by a second reconstruction processor 130, thus providing improved intermediate and/or composite image generation speeds through efficient allocation of processing tasks. As each of the intermediate and composite image volumetric outputs are generated through one of the two temporally parallel reconstructor processors 130, this provides for improved reconstruction times over other reconstruction techniques that rely upon only one reconstructor to process all PET event data.

Where the first portion reconstruction path 220/222/224/226 generates and provides the corrected fast image output comprising the image element correction factors to the composite image error correction step 236 for use directly in generation of a corrected composite image for display in step 238, it is preferred that step 226 be completed in advance of the composite image error correction step 236 to provide faster composite image display times, although not required.

In another aspect of the invention, in order to further reduce total fast intermediate image generation times different configurations may be provided. For example, the first portion fast intermediate image path steps 220/222/224/226/228 may be configured to generate a relatively faster and "smoother" lower definition image, as compared to a slower and "sharper" definition composite image generated by the composite image path steps 230/232/234/236/238. Also, where the process is performed upon a system comprising shared processing resources, one or more of the first portion fast intermediate image path steps 220/222/224/226/228 may be assigned resource priority to ensure faster first portion image generation times relative to one or more of the composite image path steps 230/232/234/236/238.

Thus the present invention is by no means limited to the specific embodiments and reconstruction processes illustrated above, and other embodiments and reconstruction process implementations will be readily apparent to one skilled in the art. The scope of the invention, therefore, is only to be limited by the following claims and the equivalent thereof.

The invention claimed is:

1. A method, comprising the steps of:
   selecting a first portion of list mode event data comprising a first quantity of annihilation events detected during a positron emission tomography scan, wherein the first quantity is greater than one, and the first quantity is determined prior to the selection of the first list mode even data portion;
   applying a list-based reconstruction technique generating first list mode event data portion thereby generating a first portion of tomographic data;
   generating an image indicative of the first portion tomographic data;
   displaying the image indicative of the first portion of tomographic data;
   applying a list-based reconstruction technique to at least one of the first list mode event data portion and the first portion of tomographic data, as well as to a second portion of the list mode event data comprising a second quantity of annihilation events detected during the positron emission tomography scan, wherein the second quantity is greater than one, thereby generating a composite tomographic data;

generating an image indicative of the composite tomographic data; and displaying the image indicative of the composite tomographic data.

2. The method of claim 1 wherein the first quantity is determined responsive to at least one parameter selected from the group consisting of an image definition specification, an image generation time constraint, and a TOF variance improvement factor.

3. The method of claim 1 wherein a sum of the first quantity and the second quantity is less than a total quantity of the positron annihilation events.

4. The method of claim 3, further comprising the step of determining the second quantity responsive to at least one parameter selected from the group consisting of an image definition specification, an image generation time constraint, and a TOF variance improvement factor.

5. The method of claim 4 further comprising the step of determining the first quantity responsive to at least one of the second quantity and at the at least one selected second portion event quantity parameter.

6. The method of claim 4 further comprising the step of determining the second responsive to at least one of the first quantity and a selected first portion event quantity parameter.

7. The method of claim 1 wherein the step of generating composite tomographic data further comprises the steps of:
using the first portion tomographic data as an initial image estimate; and
updating the initial image estimate by using the second list mode event data portion.

8. The method of claim 1, further comprising the step of evaluating the first portion tomographic data image to generate one or more correction factors;
wherein the steps of generating composite tomographic data and generating the composite image are performed by using the one or more correction factors.

9. The method of claim 1, wherein the second list mode event data portion is selected solely from a remainder of positron annihilation events not selected for the first list mode event data portion.

10. A system, comprising:
a list-based reconstructor means for selecting a first portion of list mode event data comprising a first quantity of annihilation events detected during a positron emission tomography scan, wherein the first quantity is greater than one, and the first quantity is determined prior to the selection of the first list mode event data portion, and for operating on the first list mode event data portion thereby generating a first portion of tomographic data; and
a display means for generating and displaying an image indicative of the first portion of tomographic data;
wherein the list-based reconstructor means is further configured to operate on at least one of the first list mode event data portion and the first portion of tomographic data, as well as on a second portion of the list mode event data comprising a second quantity of annihilation events detected during the positron emission tomography scan, wherein the second quantity is greater than one, to generate composite tomographic data; and
the display means is further configured to generate and display a composite image indicative of the composite tomographic data.

11. The system of claim 10 wherein the list-based reconstructor means is further configured to determine the first quantity responsive to at least one parameter selected from the group consisting of an image definition specification, an image generation time constraint, and a TOF variance improvement factor.

12. The system of claim 10 wherein a sum of a first quantity and the second quantity is less than a total quantity of the positron annihilation events.

13. The system of claim 12 wherein the list-based reconstructor means is further configured to determine the second quantity responsive to at least one parameter selected from the group consisting of an image definition specification, an image generation time constraint, and a TOF variance improvement factor.

14. The system of claim 13 wherein the list-based reconstructor means is further configured to determine the first quantity responsive to at least one of the second quantity and at least one selected portion event quantity parameter.

15. The system of claim 13 wherein the list-based reconstructor means is further configured to determine the second quantity responsive to at least one of the first quantity and a selected first portion even quantity parameter.

16. The system of claim 10 wherein the list-based reconstructor means is further configured to generate the composite tomographic data by using the first portion tomographic data as an initial image estimate and updating the initial image estimate by using the second list mode event data portion.

17. The system of claim 10 wherein the second list mode event data portion is selected solely from a remainder of the positron annihilation events not selected for the first list mode event data portion.

18. An article of manufacture comprising a non-transitory computer readable media encoded with a computer program, wherein the computer program, when implemented on a computer, causes the computer to:
select a first portion of list mode event data comprising a first quantity of annihilation events detected during a positron emission tomography scan, wherein the first quantity is greater than one, and the first quantity is determined prior to the selection of the first list mode data portion;
apply a list-based reconstruction technique to the first list mode event data portion, thereby generating a first portion of tomographic data;
generate and display an image indicative of the first portion of tomographic data;
apply a list-based reconstruction technique to least one of the first list mode event data portion and the first portion of tomographic data, as well as to a second portion of the list mode event data comprising a second quantity of annihilation events detected during the positron emission tomography scan, wherein the second quantity is greater than one, to generate composite tomographic data; and
generate and display a composite image indicative of the composite tomographic data.

19. The article of manufacture of claim 18, wherein the computer program, when implemented on the computer, causes the computer to further: determine the first quantity responsive to at least one parameter selected from the group consisting of an image definition specification, an image generation time constraint, and a TOF variance improvement factor.

20. The article of manufacture of claim 18, wherein the computer program, when implemented on the computer, wherein a sum of the first quantity and the second quantity is less than a total quantity of the positron annihilation events.

21. The article of manufacture of claim 20, wherein the computer program, when implemented on the computer, causes the computer to further: determine the second quantity responsive to at least one parameter selected from the group consisting of an image definition specification, an image generation time constraint, and a TOF variance improvement factor.

22. The article of manufacture of claim 21, wherein the computer program, when implemented on the computer, causes the computer to further determine the first quantity responsive to at least one of the second quantity and the at least one selected second portion event quantity parameter.

23. The article of manufacture of claim 18, wherein the computer program, when implemented on the computer, causes the computer to further generate the composite tomographic data by using the first portion of tomographic data as an initial image estimate and updating the initial image estimate by using the second list mode event data portion.

24. A method, comprising the steps of:
    selecting a first portion of list mode event data comprising a first quantity of annihilation events detected during a positron emission tomography scan, wherein the first quantity is greater than one, and the first quantity is determined prior to the selection of the first list mode event data portion;
    applying a list-based reconstruction technique to the first list mode event data portion, thereby generating a first portion of tomographic data;
    generating an image indicative of the first portion of tomographic data;
    viewing the image indicative of the first portion of tomographic data in substantially real time;
    applying a list-based reconstruction technique to at least one of the first list mode event data portion and the first portion of tomographic data, as well as to a second portion of the list mode event data comprising a second quantity of annihilation events detected during the positron emission tomography scan, wherein the second quantity is greater than one, thereby generating a composite tomographic data; and
    generating an image indicative of the composite tomographic data.

* * * * *